United States Patent
O'Rear et al.

(10) Patent No.: US 9,199,898 B2
(45) Date of Patent: Dec. 1, 2015

(54) PROCESS, METHOD, AND SYSTEM FOR REMOVING HEAVY METALS FROM FLUIDS

(71) Applicants: Dennis John O'Rear, Petaluma, CA (US); Russell Evan Cooper, Martinez, CA (US); Feng-Ran Sheu, Sugar Land, TX (US); Jordan Taylor Belue, Houston, TX (US)

(72) Inventors: Dennis John O'Rear, Petaluma, CA (US); Russell Evan Cooper, Martinez, CA (US); Feng-Ran Sheu, Sugar Land, TX (US); Jordan Taylor Belue, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/013,843

(22) Filed: Aug. 29, 2013

(65) Prior Publication Data

US 2014/0066683 A1  Mar. 6, 2014

Related U.S. Application Data (60) Provisional application No. 61/694,926, filed on Aug. 30, 2012.

(51) Int. Cl.

| C07C 7/152 | (2006.01) |
|---|---|
| C10G 29/04 | (2006.01) |
| C10G 21/22 | (2006.01) |
| C10L 3/10 | (2006.01) |

(52) U.S. Cl.
CPC ............... *C07C 7/152* (2013.01); *C10G 21/22* (2013.01); *C10L 3/101* (2013.01); *C10L 3/107* (2013.01)

(58) Field of Classification Search
CPC .......... C07C 7/152; C10G 29/04; C10G 29/00
See application file for complete search history.

(56) References Cited

U.S. PATENT DOCUMENTS

| 4,591,490 A | 5/1986 | Horton |
| 4,693,731 A | 9/1987 | Tarakad |
| 4,701,212 A | 10/1987 | Yan |
| 4,708,853 A | 11/1987 | Matviya |
| 4,709,118 A | 11/1987 | Yan |
| 4,764,219 A | 8/1988 | Yan |
| 4,814,152 A | 3/1989 | Yan |
| 4,874,525 A | 10/1989 | Markovs |
| 4,892,567 A | 1/1990 | Yan |

(Continued)

OTHER PUBLICATIONS

Majid Abedinzadegan Abdi et al., "Amine Degradation: Problems, Review of Research Achievements, Recovery Techniques," 14 pages, Jan. 2000.

(Continued)

*Primary Examiner* — Tam M Nguyen (57) ABSTRACT

A method for concurrently transporting and removing trace amount levels of heavy metals such as mercury from produced fluids such as natural gas, with the injection of a complexing agent and a hydrate inhibitor into the pipeline for use in transporting the produced fluid. Volatile mercury in the natural gas is removed while the produced fluid is being transported in the pipeline, with the hydrate inhibitor suppressing or decreasing the formation of the hydrate that would cause plugging in the pipeline. The complexing agent reacts with the volatile mercury in the natural gas, forming precipitate or soluble mercury complexes in the aqueous phase. The aqueous phase containing the hydrate inhibitor, unreacted complexing agent, and mercury complexes is subsequently recovered and can be re-used in the pipeline.

23 Claims, 1 Drawing Sheet

(56) References Cited

U.S. PATENT DOCUMENTS

| | | |
|---|---|---|
| 4,895,708 A | 1/1990 | Yan |
| 4,909,926 A | 3/1990 | Yan |
| 4,962,276 A | 10/1990 | Yan |
| 4,982,050 A | 1/1991 | Gammie |
| 5,034,203 A | 7/1991 | Audeh |
| 5,053,209 A | 10/1991 | Yan |
| 5,141,724 A | 8/1992 | Audeh |
| 5,190,908 A | 3/1993 | Audeh |
| 5,223,145 A | 6/1993 | Markovs |
| 5,271,760 A | 12/1993 | Markovs |
| 5,281,258 A | 1/1994 | Markovs |
| 5,281,259 A | 1/1994 | Markovs |
| 5,300,137 A | 4/1994 | Weyand |
| 5,322,628 A | 6/1994 | Yan |
| 5,338,444 A | 8/1994 | Van Buren |
| 5,354,357 A | 10/1994 | Markovs |
| 5,384,040 A | 1/1995 | Mank |
| 5,401,393 A | 3/1995 | Whitehurst |
| 5,419,884 A | 5/1995 | Weekman |
| 5,695,726 A | 12/1997 | Lerner |
| 5,989,506 A | 11/1999 | Markovs |
| 6,248,217 B1 | 6/2001 | Biswas |
| 6,268,543 B1 | 7/2001 | Sakai |
| 6,475,451 B1 | 11/2002 | Leppin |
| 6,537,443 B1 | 3/2003 | Frankiewicz |
| 6,576,092 B2 | 6/2003 | Granite |
| 6,579,507 B2 | 6/2003 | Pahlman |
| 6,685,824 B2 | 2/2004 | Frankiewicz |
| 6,719,828 B1 | 4/2004 | Lovell |
| 6,770,250 B2 | 8/2004 | Cooper |
| 6,790,420 B2 | 9/2004 | Breen |
| 6,848,374 B2 | 2/2005 | Srinivasachar |
| 6,863,005 B2 | 3/2005 | Lanier |
| 6,872,370 B2 | 3/2005 | Cooper |
| 6,953,494 B2 | 10/2005 | Nelson, Jr. |
| 6,974,564 B2 | 12/2005 | Biermann |
| 7,033,548 B2 | 4/2006 | Pahlman |
| 7,052,661 B1 | 5/2006 | Malone |
| 7,060,233 B1 | 6/2006 | Srinivas |
| 7,381,388 B2 | 6/2008 | Cooper |
| 7,476,365 B2 | 1/2009 | Al-Faqeer |
| 7,497,172 B2 | 3/2009 | Breen |
| 7,504,081 B2 | 3/2009 | Lissianski |
| 7,544,339 B2 | 6/2009 | Lissianski |
| 7,556,672 B2 | 7/2009 | Jadhav |
| 7,563,360 B2 | 7/2009 | Yamaguchi |
| 7,572,419 B2 | 8/2009 | Cooper |
| 7,597,864 B2 | 10/2009 | Breen |
| 7,615,101 B2 | 11/2009 | Holmes |
| 7,628,969 B2 | 12/2009 | Holmes |
| 7,666,318 B1 | 2/2010 | Lehtinen |
| 7,771,700 B2 | 8/2010 | Mauldin |
| 7,833,315 B2 | 11/2010 | Lissianski |
| 7,837,962 B2 | 11/2010 | Eiteneer |
| 7,901,486 B2 | 3/2011 | Cross |
| 7,901,585 B1 | 3/2011 | Lehtinen |
| 7,955,577 B2 | 6/2011 | Comrie |
| 7,968,063 B2 | 6/2011 | Shibuya |
| 8,017,550 B2 | 9/2011 | Chao |
| 8,025,160 B2 | 9/2011 | Wang |
| 8,034,246 B2 | 10/2011 | Gustafsson |
| 8,080,156 B2 | 12/2011 | Cross |
| 8,105,423 B2 | 1/2012 | Alper |
| 8,192,528 B2 | 6/2012 | Al-Faqeer |
| 8,282,707 B2 | 10/2012 | Bresler |
| 8,312,822 B2 | 11/2012 | Holmes |
| 8,382,881 B2 | 2/2013 | Bhasin |
| 8,492,509 B2 | 7/2013 | Wang |
| 8,501,128 B2 | 8/2013 | Comrie |
| 8,535,422 B2 | 9/2013 | Via |
| 8,569,205 B2 | 10/2013 | Kuhel |
| 8,598,072 B2 | 12/2013 | Sato |
| 2002/0168302 A1 | 11/2002 | Pahlman |
| 2003/0047440 A1 | 3/2003 | Granite |
| 2003/0103882 A1 | 6/2003 | Biermann |
| 2003/0116475 A1 | 6/2003 | Frankiewicz |
| 2003/0118493 A1 | 6/2003 | Cooper |
| 2003/0143128 A1 | 7/2003 | Lanier |
| 2003/0147793 A1 | 8/2003 | Breen |
| 2004/0003716 A1 | 1/2004 | Nelson, Jr. |
| 2004/0081606 A1 | 4/2004 | Cooper |
| 2004/0134396 A1 | 7/2004 | Lanier |
| 2004/0223896 A1 | 11/2004 | Cooper |
| 2004/0244657 A1 | 12/2004 | Srinivaschar |
| 2005/0129600 A1 | 6/2005 | Lanier |
| 2005/0161370 A1 | 7/2005 | Carnell |
| 2005/0167335 A1 | 8/2005 | Yamaguchi |
| 2005/0274307 A1 | 12/2005 | Lissianski |
| 2006/0011115 A1 | 1/2006 | Breen |
| 2006/0051270 A1 | 3/2006 | Brunette |
| 2006/0120934 A1 | 6/2006 | Lanier |
| 2007/0051239 A1 | 3/2007 | Holmes |
| 2007/0156288 A1 | 7/2007 | Wroblewski |
| 2007/0234902 A1 | 10/2007 | Fair |
| 2007/0246401 A1 | 10/2007 | Al-Faqeer |
| 2008/0028932 A1 | 2/2008 | Biermann |
| 2008/0041227 A1 | 2/2008 | Mulvaney, III |
| 2008/0056973 A1 | 3/2008 | Schofield |
| 2008/0121142 A1 | 5/2008 | Comrie |
| 2008/0241027 A1 | 10/2008 | Lissianski |
| 2008/0241029 A1 | 10/2008 | Lissianski |
| 2008/0302730 A1 | 12/2008 | Wang |
| 2009/0007785 A1 | 1/2009 | Kimura |
| 2009/0029447 A1 | 1/2009 | Squire |
| 2009/0032472 A1 | 2/2009 | Krogue |
| 2009/0071073 A1 | 3/2009 | Al-Faqeer |
| 2009/0104097 A1 | 4/2009 | Dunson, Jr. |
| 2009/0145343 A1 | 6/2009 | Mauldin |
| 2009/0155148 A1 | 6/2009 | Kanazirev |
| 2009/0211444 A1 | 8/2009 | Lissianski |
| 2009/0235848 A1 | 9/2009 | Eiteneer |
| 2009/0272267 A1 | 11/2009 | Nelson |
| 2010/0000409 A1 | 1/2010 | Alper |
| 2010/0025184 A1 | 2/2010 | Shibuya |
| 2010/0025302 A1 | 2/2010 | Sato |
| 2010/0032345 A1 | 2/2010 | Cross |
| 2010/0083830 A1 | 4/2010 | Cross |
| 2010/0126909 A1 | 5/2010 | Bhasin |
| 2010/0147745 A1 | 6/2010 | Den Boestert |
| 2010/0251938 A1 | 10/2010 | Comrie |
| 2011/0000855 A1 | 1/2011 | Kuhel |
| 2011/0174016 A1 | 7/2011 | Carnell |
| 2011/0203499 A1 | 8/2011 | Comrie |
| 2011/0223088 A1 | 9/2011 | Chang |
| 2011/0226700 A1 | 9/2011 | Hetherington |
| 2011/0226989 A9 | 9/2011 | Seeker |
| 2011/0312491 A1 | 12/2011 | Chao |
| 2011/0315013 A1 | 12/2011 | Wang |
| 2012/0000359 A1 | 1/2012 | Bresler |
| 2012/0017639 A1 | 1/2012 | Peterson |
| 2012/0103912 A1 | 5/2012 | Hetherington |
| 2012/0121485 A1 | 5/2012 | Rogers |
| 2012/0272877 A1 | 11/2012 | Comrie |
| 2012/0322696 A1 | 12/2012 | Hayes |
| 2013/0034479 A1 | 2/2013 | Holmes |
| 2013/0090505 A1 | 4/2013 | Catchpole |
| 2013/0139526 A1 | 6/2013 | Jariwala |
| 2013/0152788 A1 | 6/2013 | Turbeville |
| 2013/0168293 A1 | 7/2013 | O'Rear |
| 2013/0213223 A1 | 8/2013 | Posa |
| 2013/0272936 A1 | 10/2013 | Nalepa |
| 2013/0306310 A1 | 11/2013 | Gallup |
| 2013/0306311 A1 | 11/2013 | Cooper |
| 2013/0306312 A1 | 11/2013 | O'Rear |
| 2013/0306521 A1 | 11/2013 | O'Rear |

OTHER PUBLICATIONS

Peter J.H. Carnell, et al. "Mercury matters," Reprinted from Hydrocarbon Engineering, 3 pages, Dec. 2005.

S. Chiarle et al., "Mercury Removal From Water by Ion Exchange Resins Adsorption," *Wat. Res.* vol. 34, No. 11, pp. 2971-2978, 2000.

(56) References Cited

OTHER PUBLICATIONS

Jeriffa De Clercq, "Removal of mercury from aqueous solutions by adsorption on a new ultra stable mesoporous adsorbent and on a commercial ion exchange resin," International Journal of Industrial Chemistry (IJIC), 6 pages, 2012.

DOW Brochure, Technical Information—Gas Treating Products & Services, Form No. 170-00284-0704, 4 pages, Jul. 2004.

Randy Haws, "Contaminants in Amine Gas Treating," CCR Technologies Inc., 13 pages.

Hong Meng et al., "Removal of heat stable salts from aqueous solutions of N-methyldiethanolamine using a specially designed three-compartment configuration electrodialyzer," *Journal of Membrane Science* 322, 2008, pp. 436-440.

Y. Song et al., "Effect of $O_2$ and Temperature on Sour Corrosion" ISSN 0010-9312, NCAE International, Jul. 2012, 10 pages.

James G. Speight, "Petroleum Refinery Processes," Kirk-Othmer Encyclopedia of Chemical Technology, John Wiley & Sons, Inc. Aug. 19, 2005, 49 pages.

John C. Polasek et al., "Using Mixed Amine Solutions for Gas Sweetening" Bryan Research & Engineering, Inc., 2006, 10 pages.

James A. Anabtawi, et al., "Reaction of Trace Mercury in Natural Gas with Dilute Polysulfide Solutions in a Packed Column," *Ind. Eng. Chem. Res.*, 1991, 30 pp. 2592-2595.

Vince Atma Row et al., "The impact of mercury on gas processing plant assets and its removal," Johnson Matthey Catalysts Process Catalysts and Technologies, 8 pages—presented at Spring Conference 2011—May 26, 2011.

PROCESS, METHOD, AND SYSTEM FOR REMOVING HEAVY METALS FROM FLUIDS

CROSS-REFERENCE TO RELATED APPLICATIONS

This application claims benefit under 35 USC 119 of U.S. Provisional Patent Application No. 61/694,926 with a filing date of Aug. 30, 2012.

TECHNICAL FIELD

The invention relates generally to a process, method, and system for removing heavy metals such as mercury from hydrocarbon fluids such as natural gas.

BACKGROUND

Heavy metals can be present in trace amounts in all types of produced fluids such as natural gases and crude oils. The amount can range from below the analytical detection limit to several thousand ppbw (parts per billion by weight) depending on the source. In the case of natural gas and natural gas liquids, it is likely to be present as elemental mercury; whilst in crude oil it may also be present as mercuric sulfide (meta-cinnabar) and or organo-metallic and ionic mercury.

Methods have been disclosed to remove heavy metals such as mercury from produced fluids. US Patent Publication No. 2011/0253375 discloses an apparatus and related methods for removing mercury from reservoir effluent by placing materials designed to adsorb mercury into the vicinity of a formation at a downhole location, and letting the reservoir effluent flow through the volume of the adsorbing material. US Patent Publication No. 2012/0073811 discloses a method for mercury removal by injecting a solid sorbent into a wellbore intersecting a subterranean reservoir containing hydrocarbon products.

Other common approaches utilize treatments for the fluids once the fluids are recovered from subterranean reservoirs and brought to a surface production installation. U.S. Pat. No. 4,551,237 discloses the use of an aqueous solution of sulfide materials to remove arsenic from oil shale. U.S. Pat. No. 4,877,515 discloses a process for removing mercury from hydrocarbon streams, gas or liquid. U.S. Pat. No. 4,915,818 discloses a method of removing mercury from liquid hydrocarbons (natural gas condensate) by contact with a dilute aqueous solution of alkali metal sulfide salt. U.S. Pat. No. 6,268,543 discloses a method for removing elemental mercury with a sulfur compound. U.S. Pat. No. 6,350,372 discloses removing mercury from a hydrocarbon feed by contact with an oil soluble or oil miscible sulfur compound U.S. Pat. No. 4,474,896 discloses using polysulfide based absorbents to remove elemental mercury) ($Hg^0$) from gaseous and liquid hydrocarbon streams.

There is still a need for improved methods and systems to remove heavy metals, particularly mercury, from fluids such as natural gas and upstream from the processing plant if possible.

SUMMARY

In one aspect, the invention relates to a method for concurrently transporting and removing a trace amount of volatile mercury in a natural gas stream extracted from a subterranean formation. The method comprises: obtaining a produced fluid containing the natural gas and produced water from the subterranean formation; transporting the produced fluid in a pipeline extending from a well head above the subterranean formation to a production facility; injecting into the pipeline an effective amount of a hydrate inhibitor and a complexing agent for a treated produced fluid with a concentration of hydrate particles of less than 50 volume % and a reduced concentration of volatile mercury; wherein the complexing agent extracts volatile mercury in the natural gas forming non-volatile mercury complexes in the produced water.

DETAILED DESCRIPTION

The following terms will be used throughout the specification and will have the following meanings unless otherwise indicated.

"Trace amount" refers to the amount of mercury in the natural gas. The amount varies depending on the natural gas source, ranging from 0.01 $\mu g/Nm^3$ to up to 30,000 $\mu g/Nm^3$.

"Heavy metals" refers to gold, silver, mercury, osmium, ruthenium, uranium, cadmium, tin, lead, selenium, and arsenic. While the description described herein refers to mercury removal, in one embodiment, the treatment removes one or more of the heavy metals.

"Volatile mercury" refers to mercury that is present in the gas phase of well gas or natural gas. In one embodiment, volatile mercury comprises primarily elemental mercury) ($Hg^0$) with some dialkylmercury compounds (dimethyl mercury).

"Mercury sulfide" may be used interchangeably with HgS, referring to mercurous sulfide, mercuric sulfide, and mixtures thereof. Normally, mercury sulfide is present as mercuric sulfide with an approximate stoichiometric equivalent of one mole of sulfide ion per mole of mercury ion. Mercury sulfide is not appreciably volatile, and not an example of volatile mercury. Crystalline phases include cinnabar, metacinnabar and hypercinnabar with metacinnabar being the most common.

"Hydrates" or "hydrate particles" refers to crystals formed by water in contact with natural gases and associated liquids, as an ice-like substance, typically in a ratio of 85 mole % water to 15% hydrocarbons. Hydrates can form when hydrocarbons and water are present at the right temperature and pressure, such as in wells, flow lines, or valves. The hydrocarbons become encaged in ice-like solids which rapidly grow and agglomerate to sizes which can block flow lines. Hydrate formation most typically occurs in subsea production lines, which are at relatively low temperatures and elevated pressures. Hydrates also include solids formed by reaction of carbon dioxide and water.

"Production facility" means any facility for receiving natural gas and preparing the gas for sale. The production facility may be a ship-shaped vessel located over a subsea well site, an FPSO vessel (floating production, storage and offloading vessel) located over or near a subsea well site, a near-shore separation facility, or an onshore separation facility. Synonymous terms include "host production facility" or "gathering facility."

"Pipeline" may be used interchangeably with "production line," referring to a riser and any other pipeline used to transport production fluids to a production facility. The pipeline may include, for example, a subsea production line and a flexible jumper.

"Produced water" refers to the water generated in the production of oil and/or natural gas, including formation water (water present naturally in a reservoir, or water that leaves the well as a liquid), condensed water (water that leaves the well as a gas and subsequently condenses in the production line), as well as water previously injected into a formation either by matrix or fracture injection, which can be any of connate water, aquifer water, seawater, desalinated water, industrial by-product water, and combinations thereof.

"Produced fluids" refers the mixture of hydrocarbons, e.g., natural gas, some crude oil, hydrocarbon condensate, and produced water that is removed from a geologic formation via a production well.

"Subsea production system" means an assembly of production equipment placed in a marine body. The marine body may be an ocean environment or a fresh water lake. Similarly, "subsea" includes both an ocean body and a deepwater lake.

Generally, natural gas streams comprise low molecular weight hydrocarbons such as methane, ethane, propane, other paraffinic hydrocarbons that are typically gases at room temperature, etc. Mercury is present in natural gas as volatile mercury, including elemental mercury $Hg^0$, in levels ranging from about 0.01 $\mu g/Nm^3$ to 30,000 $\mu g/Nm^3$. The mercury content may be measured by various conventional analytical techniques known in the art, including but not limited to cold vapor atomic absorption spectroscopy (CV-AAS), inductively coupled plasma atomic emission spectroscopy (ICP-AES), X-ray fluorescence, or neutron activation. If the methods differ, ASTM D 6350 is used to measure the mercury content.

Depending on the source or sources of the natural gas, in addition to mercury, the stream can have varying amount of (produced) water ranging from 0.1 to 90 vol. % water in one embodiment, from 5 to 70 vol. % water in a second embodiment, and from 10-50 vol. % water in a third embodiment. The volume percents are calculated at the temperature and pressure of the pipeline.

Natural gas is often found in wells located in remote locations and must be transported from the wells to developed locations for use. This can be done by a production line, or by conversion of the methane in the natural gas into Liquefied Natural Gas (LNG) for transport. Natural gas pipelines can be clogged with gas hydrates. The hydrates can be methane-water hydrates, carbon dioxide-water hydrates, or other solid hydrates. Hydrates can also be found in gas exploration at ocean depths. At a depth such as 500 m, the pressure is about 50 atmospheres, and the temperature 4-5° C., it is ideal for gas hydrate formation. Gas hydrates also exist in permafrost regions near the surface of places such as Alaska, in sedimentary formations where hydrocarbons, water, and low temperatures are found.

In offshore production, the conditions conducive to hydrate formation commonly occur during transient operations (shutdown and restart conditions) due to low temperatures, but can occur under steady-state production conditions (typical of long subsea tiebacks). Hydrate formation can restrict flow and even form a solid plug to block all production in a short time period. Hydrate inhibitors have been used to solve the hydrate formation problem by depressing both the hydrate and freezing temperatures.

The invention relates to an improved method and a system to remove heavy metals such as mercury present in natural gas feedstock. The mercury removal is carried out concurrently with the process to manage the hydrate formation, e.g., with the injection of a hydrate inhibitor into a pipeline. The invention also relates to a method for concurrently transporting and removing heavy metals such as mercury contained in natural gas by pipeline reaction, wherein mercury removal reaction occurs in the course of transferring natural gas through a pipeline and the inhibition of hydrate formation in the pipeline.

Concurrent Mercury Removal & Inhibiting Hydrate Formation

In one embodiment, a complexing agent is added to the pipeline along with a hydrate inhibitor. The complexing agent refers to a material or compound that is capable of converting volatile mercury in the natural gas into a form which is not volatile. The complexing agent can be added in the same feed line with the hydrate inhibitor, or as a separate feed by itself. The addition of the complexing agent can be continuous or intermittent. The complexing agent can be added to a pipeline at the well head, into a manifold, intermediate locations between the production well and a processing facility, into at least a location downhole in the wellbore, or combinations of the above.

In one embodiment, the complexing agent is introduced (injected) into the pipeline at an entry point at the wellhead or close to the well head, e.g., within 1000 ft, within 500 ft, or within 100 ft of the well head, along with a hydrate inhibitor or separately by itself. In yet another embodiment, the complexing agent is introduced at intervals in the pipeline carrying the natural gas from the well head to a processing facility, for the reaction to remove the mercury to take place in the pipeline before the natural gas reaches its destination. The hydrate inhibitor to be added to the pipeline along with the complexing agent can be any hydrate inhibitor commonly known in the art, e.g., a thermodynamic inhibitor (TI) or a low dosage hydrate inhibitor (LDHI) or sometimes called "threshold inhibitor."

In one embodiment, a sufficient amount of hydrate inhibitor(s) (TIs and/or LDHIs) is added to the production along with the complexing agent to shift the hydrate equilibrium, decrease the rate at which the hydrate forms, or prevent agglomeration of hydrates, for a concentration of hydrate particles of <60 vol. %. The injection of the hydrate inhibitor helps prevent plugs in the pipeline. In another embodiment, a sufficient amount is added for a concentration of hydrate particles of <50 vol. %.

The mercury removal with a complexing agent is carried out concurrently with the treatment with a thermodynamic inhibitor (TI) in concentrations of 5-80 vol. % of the water (produced water) in the produced fluid containing natural gas in one embodiment, and in an amount ranging from 30-60 vol. % in a second embodiment. TI refers to a molecule/compound, or mixtures thereof, capable of reducing the hydrate formation temperature, e.g., by 0.5 to about 30° C. Examples of TI include but are not limited to potassium formate, monoethylene glycol (MEG), a diethylene glycol, a triethylene glycol, a tetraethylene glycol, a propylene glycol, a dipropylene glycol, a tripropylene glycol, a tetrapropylene glycol, a polyethylene oxide, a polypropylene oxide, a copolymer of ethylene oxide and propylene oxide, a polyethylene glycol ether, a polypropylene glycol ether, a polyethylene oxide glycol ether, a polypropylene oxide glycol ether, a polyethylene oxide/polypropylene oxide glycol ether, a monosaccharide, a methylglucoside, a methylglucamine, a disaccharide, fructose, glucose, an amino acid, an amino sulfonate, methanol, ethanol, propanol, isopropanol, and combinations thereof. Further details regarding inhibitors are described in U.S. Pat. Nos. 6,080,704, 6,165,945, 6,080,704, 6,225,263, 5,076,364, 5,076,373, 5,083,622, 5,085,282, 5,248,665 the relevant disclosures with respect to the compositions and methods of using thereof are included herein by reference. When the gas arrives at its destination, a portion of the TI can be recovered as a liquid phase and returned to the well site.

In one embodiment and concurrently with the mercury removal by a complexing agent, a low dosage hydrate inhibitor (LDHI) is employed in an amount of 0.5-5.0 vol. % of the (produced) water present in the produced fluid containing the natural gas. LDHI refers to a molecule/compound, or mixtures thereof, capable of any of: decreasing the rate of hydrate formation; keeping the hydrate from forming for a period of time; and allowing for hydrates to form, but preventing them from adhering to each other by keeping the hydrate crystals in a slurry. Examples of LDHI include but are not limited to oxazolidinium compounds, tertiary amine salts, reaction products of non-halide-containing organic acids and organic amines, polymers having n-vinyl amide and hydroxyl moieties, dendrimeric or branched compounds, linear polymers and copolymers, grafted or branched linear polymers and copolymers, onium compounds, and combinations thereof. Further details regarding LDHI are described in U.S. Pat. Nos. 7,615,102, 6,107,531, 6,180,699; US Patent Publication No. 20120172604, 20120190893, 20120161070, 20120078021, 20120077717, the relevant disclosures with respect to the compositions and methods of using thereof are included herein by reference.

In another embodiment and concurrently with the mercury removal by a complexing agent, a hydrate inhibitor mixture of one or more TI and one or more LDHI is used for a synergistic effect. When the gas arrives at its destination, the mixture of the TI and LDHI can be recovered and recycled. Further details regarding a synergistic mixture of TI and LDHI are described in U.S. Pat. No. 7,994,374, the relevant disclosures with respect to the compositions and methods of using thereof are included herein by reference.

Examples of complexing agents for the removal of mercury include but are not limited to mercaptans, organic polysulfides (compounds of the general formula R—$S_x$—R', where x is greater than 1 and R and R' are alkyl or aryl groups), sulfanes (compounds of the formula $H_2S_x$ where x is greater than 1), water-soluble sulfur species, e.g., sulfides, hydrosulfides, and inorganic polysulfides, and combinations thereof, for extracting volatile mercury in natural gas into the liquid phase forming non-volatile mercury complexes. Examples of non-volatile mercury complexes include precipitate (e.g., HgS) or soluble mercury sulfur compounds (e.g. $HgS_2^{2-}$). Examples of water-soluble sulfur compounds include sodium polysulfide, ammonium polysulfide, calcium polysulfide, sodium hydrosulfide, potassium hydrosulfide, ammonium hydrosulfide, sodium sulfide, potassium sulfide, calcium sulfide, magnesium sulfide, ammonium sulfide, sodium thiocarbamate, sodium dithiocarbamate, ammonium thiocarbamate, ammonium dithiocarbamate and mixtures thereof. Aqueous source containing water-soluble sulfur species can be any of sulfidic water, sulfidic waste water, kraft caustic liquor, kraft carbonate liquor, etc.

Preferably, the complexing agent is soluble in the hydrate inhibitor employed. For example, with the use of a TI such as MEG and/or methanol, an inorganic polysulfide is employed. In one embodiment, the complexing agent is sodium polysulfide, for an extraction of mercury from the natural gas according to equation: $Hg(g)+Na_2S_x(aq) \rightarrow HgS(aq)+Na_2S_{x-1}(aq)$, where (g) denotes the mercury in the gas phase and (aq) denotes a species in water. In another embodiment, the mercury complexing agent is mercaptan containing five or more carbons and disulfides.

The amount of complexing agents to be added to the pipeline for mercury removal is determined by the effectiveness of complexing agent employed. The amount is at least equal to the amount of mercury in the natural gas on a molar basis (1:1), if not in an excess amount. In one embodiment, the molar ratio ranges from 2:1 (mol complexing agent:mol mercury) to 10,000:1. In another embodiment, from 10:1 to 5000:1. In yet another embodiment, a molar ratio of sulfur additive to mercury ranging from 50:1 to 2500:1. If the mercury complexing agent is an organic polysulfide, inorganic polysulfide, sulfane or mercaptan, the moles of complexing agent are calculated on the same basis as the amount of sulfur present.

The amount of complexing agent added is limited to 5 vol. % of less of the water phase in the pipeline in one embodiment, and less than 2 vol. % in a second embodiment. In one embodiment with the use of water-soluble sulfur compounds in aqueous solution as complexing agents, a sufficient amount is added to the pipeline for a sulfide concentration ranging from 0.05 M to 10M; from 0.1M to 5M in a second embodiment; from 0.3M to 4M in a third embodiment; and at least 0.5M in a fourth embodiment.

With the addition of complexing agent to the pipeline, volatile mercury is extracted from the gas phase into the aqueous phase containing the hydrate inhibitor, for a treated gas stream having a reduced concentration mercury of less than 50% of the original mercury level in the natural gas (at least 50% mercury removal). In another embodiment, the treated gas contains less than 25% of the original mercury level (at least 75% removal). In a third embodiment, less than 10% of the original level (at least 90% removal). The mercury content in the treated gas stream will depend on the mercury content of the feed and the complexing agent employed.

Optional Additives:

In one embodiment in addition to the complexing agent, at least one of an anti-foam and/or a demulsifier is added to the pipeline. As used herein, the term anti-foam includes both anti-foam and defoamer materials, for preventing foam from happening and/or reducing the extent of foaming. Additionally, some anti-foam material may have both functions, e.g., reducing/mitigating foaming under certain conditions, and preventing foam from happening under other operating conditions. Anti-foam agents can be selected from a wide range of commercially available products such as silicones, e.g., polydimethyl siloxane (PDMS), polydiphenyl siloxane, fluorinated siloxane, etc., in an amount of 1 to 500 ppm.

In one embodiment, at least a demulsifier is added to pipeline in a concentration from 1 to 5,000 ppm. In another embodiment, a demulsifier is added at a concentration from 10 to 500 ppm. In one embodiment, the demulsifier is a commercially available demulsifier selected from polyamines, polyamidoamines, polyimines, condensates of o-toluidine and formaldehyde, quaternary ammonium compounds and ionic surfactants. In another embodiment, the demulsifier is selected from the group of polyoxyethylene alkyl phenols, their sulphonates and sodium sulphonates thereof. In another embodiment, the demulsifier is a polynuclear, aromatic sulfonic acid additive.

Pipeline Reaction:

The pipeline is of sufficient length so that, in the course of transferring the natural gas through it, sufficient mixing of produced fluid and complexing agent occurs for reactions to take place between the complexing agent and the heavy metals. In this pipeline reaction, mercury forms soluble and/or insoluble complexes, and is extracted from the produced fluid into the water phase. In one embodiment wherein mercury reacts with the complexing agent to form insoluble complexes, the mercury complexes can then be removed by filtration, settling, or other methods known in the art, e.g., removal of solids from a gas or liquid stream to produce a hydrocarbon product with reduced mercury content. In another embodiment, mercury reacts with the complexing agent and is extracted into the hydrate inhibitor fluid as a soluble compound, the Hg-enriched water phase can be separated from the hydrocarbon fluid by means known in the art, e.g., gravity settler, coalescer, separator, etc., at a processing facility at the destination of the pipeline to produce a hydrocarbon product with reduced mercury content.

The pipeline is sufficiently long for a residence time of at least one second in one embodiment, at least 10 minutes in another embodiment, at least 30 minutes in yet another embodiment, at least 10 hours in a fourth embodiment. The pipeline can be in the range of 20-200 hours that extends for hundreds if not thousands of kilometers. In one embodiment, the reaction takes place over a relatively short pipeline, e.g., at least 10 m but 50 meters or less for intra-facility transport. In yet another embodiment, the reaction takes place in a pipeline section over a long distance transport of at least 2.5 km. In one embodiment the flow in the pipeline is turbulent, and in another embodiment the flow is laminar.

For effective removal of mercury from the produced fluids with sufficient mixing to create a dispersion of the complexing agent, the pipeline has a minimum superficial liquid velocity of at least 0.1 m/s in one embodiment; at least 0.5 m/s in a second embodiment; and at least 5 m/s in a third embodiment. In one embodiment, the natural mixing in the pipeline can be augmented with the use of mixers at the point of introduction of the complexing agent, or at intervals downstream in the pipeline. Examples include static or in-line mixers as described in Kirk-Othmer Encyclopedia of Chemical Technology, Mixing and Blending by David S. Dickey, Section 10, incorporated herein by reference.

The mercury removal in the pipeline can be land-based, located subsea, or combinations thereof, by extending from a production site to a crude processing facility, receiving production flow from a surface wellhead or other sources. Examples include subsea pipelines, where the great depth of the pipeline can make the pipeline relatively inaccessible, and where the pipelines include a header or vertical section that forms a substantial pressure head. The pipeline system can be on-shore, off-shore (as a platform, FPSO, etc), or combinations thereof. For off-shore locations, the pipeline system can be a structure rising above the surface of the water (well platform) or it can be sub-surface (on the sea bed).

In one embodiment where the production site is at a sufficient distance from the processing facility, the pipeline system includes intermediate collection and/or processing facilities. The intermediate facilities contain one or more supply tanks to dispense complexing agents and/or other process aids, e.g., hydrate inhibitors, foamants, NaOH, diluents, etc., to facilitate the flow of produced fluids in into the pipeline. In another embodiment, the intermediate facilities may also include equipment such as gravity separator, plate separator, hydroclone, coalescer, centrifuge, filter, collection tanks, etc., for the separation, storage, and treatment of recovered stream containing hydrate inhibitor(s) and complexing agent(s).

Mercury Recovery System:

In one embodiment, at the destination, the treated produced fluid is separated under conditions sufficient to provide a gas phase stream, an oil phase stream (if any), and an aqueous phase stream that contains a substantial portion of the water, hydrate inhibitor(s), and non-volatile mercury complexes. In one embodiment, up to 99% by volume of the water, hydrate inhibitors, unreacted complexing agent, and non-volatile mercury complexes are removed from the treated produced fluid stream compounds and isolated in the aqueous phase. A small portion (less than 1 vol. %) of the water, hydrate inhibitors, unreacted complexing agent and non-volatile mercury can be entrained in the gas phase and/or the oil phase stream.

The gas phase stream with a reduced concentration of mercury, e.g., less than 50 µg/Nm$^3$ in one embodiment, less than 10 µg/Nm$^3$ in a second embodiment, and less than 1 µg/Nm$^3$ in a third embodiment, can be processed as needed for consumption or sale. The processing in one embodiment includes further treatment to remove acid gas, e.g., removal of sulfur containing compounds and/or carbon dioxide. In another embodiment, the processing includes the removal of water, dehydration, by methods known in the art to produce a gas with water content suitable for sale or consumption. In yet another embodiment, the processing includes both acid gas removal and dehydration. In yet another embodiment, the processing includes further mercury removal by contact with a solid adsorbent.

The aqueous phase containing water, hydrate inhibitor(s), unreacted complexing agent(s), and non-volatile mercury complexes is further treated to separate and remove water, and for the mixture of hydrate inhibitor/unreacted complexing agent/and non-volatile mercury compounds to be re-injected back into the pipeline. Details regarding a process that can be employed for the recovery of hydrate inhibitors can be found in U.S. Pat. No. 7,994,374, the relevant disclosures of which are incorporated herein by reference.

In one embodiment, the aqueous phase stream is flashed in a column or tower at a temperature above the boiling point of water to drive water from the mixture, e.g., at a temperature above 100° C., a temperature above 120° C., at 150° C. or more. The operating pressure of the column can range from a low of about 0.5 bar to a high of about 200 bar. The overhead stream from the column can include up to 0.1 wt. % of hydrate inhibitors, up to 0.01 wt. % of the unreacted complexing agents, and less than 0.1 µg/Nm$^3$ mercury. The bottom stream from the column can include from 20 wt. % to 99 wt. % of inhibitors for a recovery of at least 99% by volume of hydrate inhibitors originally added to the pipeline. The bottom stream further comprises from 0 to 30 wt. % water, less than 0.1 wt. % of hydrate-forming compounds, up to 99 wt. % of the unreacted complexing agent, and from 50 to 99.9% of the mercury originally present in the untreated produced fluid in the form of non-volatile mercury complexes.

The bottom stream is recovered and stored in a tank for later use. Additional fresh inhibitors, complexing agents, and other additives can be added to the tank in subsequent injection into the pipeline to prevent hydrate formation, concurrently with the removal of mercury from the extracted natural gas. Mercury in the form of non-volatile mercury complexes will gradually build up over time in the recycled hydrate inhibitor stream. This mercury can be removed by processes known in the art, including but are not limited to filtration, centrifugation, precipitation, reduction to elemental mercury followed stripping, distillation, adsorption, ion exchange, or transfer to a hydrocarbon steam and separation, and combinations. Distillation at sub-atmospheric pressures and temperatures less than 200° C. can be used to recover the hydrate inhibitor as a relatively pure overhead stream. The bottoms from this sub-atmospheric distillation is a slurry containing additives, sediments, salts, and mercury complexes. Alternatively a portion of the mercury-containing hydrate inhibitor stream can be purged from the system. In one embodiment, the non-volatile mercury complexes can be removed from the regenerated/recycled hydrate inhibitor stream with the use of a mercury absorber containing a bed of sulphided absorbent as disclosed in U.S. Pat. No. 7,435,338, the relevant disclosure is incorporated herein by reference.

Figure Illustrating Embodiments:

Reference will be made to the figures to further illustrate embodiments of the invention.

Figure 1:
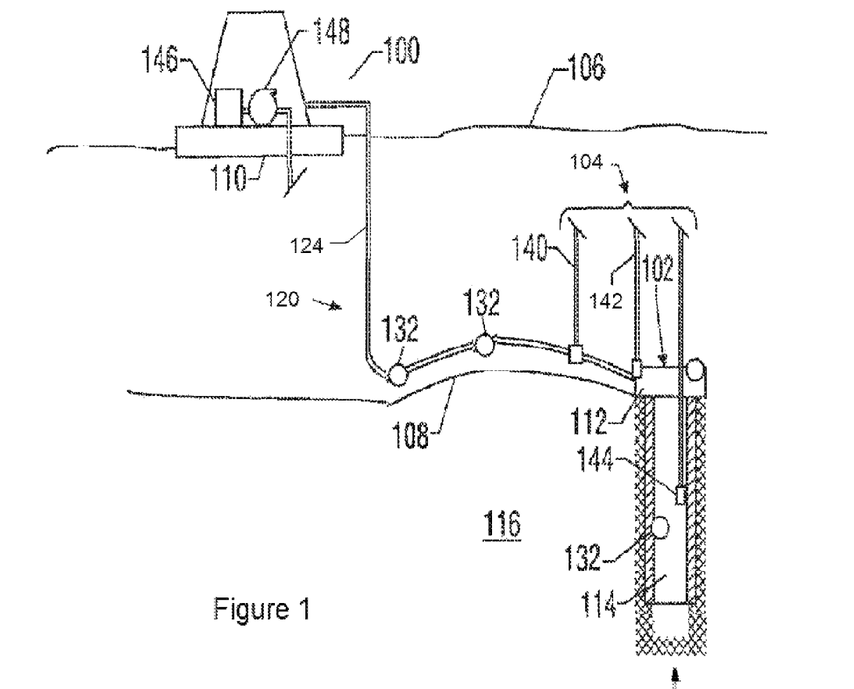
FIG. 1 is a diagram illustrating an embodiment of a system for the removal of mercury from a pipeline as natural gas is transported from a subsea well to a processing facility.

FIG. 1 is a diagram that schematically illustrates a system 104 for the removal of mercury in natural gas, as the gas is being transported from one or more subsea wells to a surface collection facility 100 such as a floating production, storage and offloading (FPSO) unit, an intermediate collection system, or a processing facility.

As shown, the system 104 is for dispensing at least a hydrate inhibitor and a complexing agent into the pipeline deployed in conjunction with the facility 100 located at a water surface 106. The dispensing system 104 services one or more subsea production wells 102 residing in a seabed 108. Each well 102 includes a wellhead 112 and related equipment positioned over a wellbore 114 formed in a subterranean formation 116. Production fluid is conveyed to a surface collection facility such as the FPSO 100 or separate structure, such as an intermediate collection and/or processing facility (not shown), via a pipeline 120. The fluid may be conveyed to the surface facility 100 in an untreated state or after being processed, at least partially, by an intermediate collection and/or processing facility (not shown). The line 120 extends directly from the wellhead 112 or from a manifold (not shown) that receives flow from a plurality of wellheads 112.

The line 120 includes a vertical section or riser 124 that terminates at the FPSO (or a processing facility) 100. The dispensing system 104 continuously or intermittently injects at least a hydrate inhibitor and/or a complexing agent into the flow line 120 or the well 102 for the removal of heavy metals.

In one embodiment, the dispensing system 104 can be utilized with one or more sensors 132 positioned along selected locations along the flow line 120 and the well 102. During production operations, the dispensing system 104 supplies (or pumps) one or more hydrate inhibitors and/or complexing agent to the flow line 120. The supply of hydrate inhibitors/complexing agents may be continuous, intermittent or actively controlled in response to sensor measurements. In one mode of controlled operation, the dispensing system 104 receives signals from the sensors 132 regarding a parameter of interest relating to a characteristic of the produced fluid, e.g., temperature, pressure, flow rate, amount of water, concentration of heavy metals in the produced fluids based on the formation of intermediate complexes, etc. Based on the data provided by the sensors 132, the dispensing system 104 determines the appropriate type and/or amount of hydrate inhibitor/complexing agents needed for the pipeline reactions to take place to reduce the formation of hydrate, the concentration of mercury, arsenic, and the like.

In embodiments, the dispensing system 104 can include one or more supply lines 140, 142, 144 that dispense hydrate inhibitors, complexing agents, other additives, etc. into the pipeline 120 separately or as a single feed line at a location close to the wellhead, or right at the wellhead 102, in a manifold (not shown) or into a location downhole in the wellbore 114, respectively. The supply tank or tanks 146 and injection units 148 can be positioned on the surface facility 110 for continuous supply to the dispensing system 104. In other embodiments, one or more of the lines 140, 142, 144 can be inside or along the pipeline 120, for dispensing of hydrate inhibitors and/or other agents into the pipeline 120.

While multiple dispensation points are shown in FIG. 1, it should be understood that a single dispensation point may be adequate. Moreover, the above-discussed locations are merely representative of the locations at which the hydrate inhibitors and complexing agents can be dispensed into the production fluid for the pipeline reactions to prevent the formation of hydrate while concurrently remove mercury. The pipeline 120 can extend on land between a production well at a remote location to a facility 100 located in a refinery or a shipping terminal.

Figure 2:
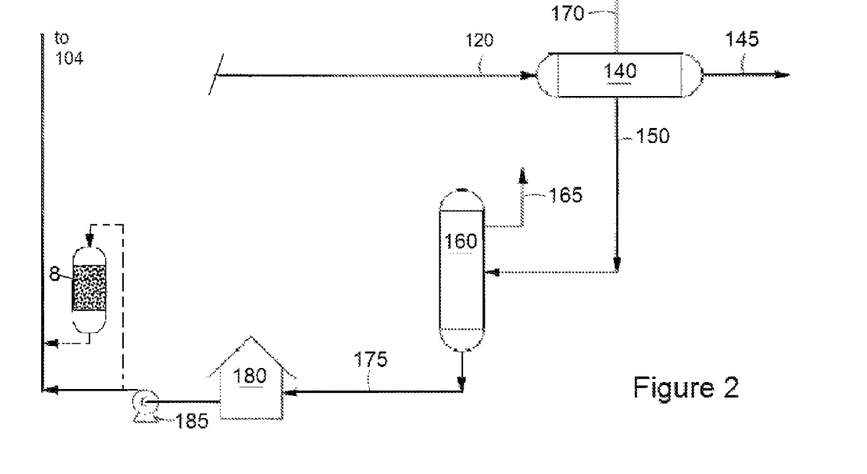
FIG. 2 is a diagram illustrating a system for the recovery/regeneration of hydrate inhibitor(s) and complexing agent(s) at the production facility, after the pipeline reaction for the removal of mercury.

In one embodiment as shown in FIG. 2, as the pipeline 120 arrives at the facility 100, the treated produced fluid in the pipe line 120 can be separated in a horizontal pressure separator 140 to provide a treated gas phase 170, an oil phase stream 145, and an aqueous stream 150. The gas phase stream 170 and the oil phase stream 145 can be processed as needed for consumption or sale.

The aqueous stream 150 can be separated in flash column 160 to remove the captured water from the mixture hydrate inhibitor(s), unreacted complexing agents, and mercury removed from the produced fluid in the form of non-volatile mercury compounds. The overhead stream 165 consists primarily of flashed water can be disposed, recycled, or injected back into an oil or gas reservoir (in production or depleted). The bottom stream 175 containing recycled/regenerated hydrate inhibitors, unreacted complexing agents, and mercury compounds can be passed to a storage container 180, which can be sent to the dispensing system 104 for subsequently feeding one or more subsea production wells 102.

In one embodiment as shown in dotted lines, mercury compounds in the recycled/regenerated hydrate inhibitor stream 185 is optionally removed by contacting the stream with a bed 8 of solid absorbent particles, e.g., comprising a sulphided metal and optionally supported on support metal, or sulphur supported on carbon, or ion exchange resin for the removal of the non-volatile mercury compounds before recycling back to dispensing system 104.

EXAMPLES

The following illustrative examples are intended to be non-limiting.

Example 1

In a three-neck flask with a Teflon stirrer (as glass reactor) was placed a 200 ml of solution of stannous chloride and sulfuric acid, for a concentration of 10% stannous chloride and 5% sulfuric acid. When mercury vapors were to be generated, 0.5 cc of a 209.8 ppm Hg solution of mercuric chloride in water was injected into the reactor via a septum. The stannous chloride rapidly reduced the mercury to elemental mercury. The glass reactor is provided with a line carrying 300 cc/min of nitrogen, which bubbled in the reducing acidic stannous chloride solution, sweeping the evolved elemental mercury to the downstream absorbers.

The glass reactor was connected to two absorbers in series, each of which contained 200 ml of solution. The absorbers were equipped with a glass frit to produce small bubbles. The bubbles contacted the absorbing solution for about one second. The first absorber contained the test solution. The second contained 3% sodium polysulfide in water. The 3% sodium polysulfide solution was prepared by dilution of a 30% solution of sodium polysulfide. This second absorber was a scrubber to remove the last traces of mercury from the nitrogen to provide mercury mass closures. Analysis of the exit gas from the second absorber by both Lumex and Jerome techniques found no detectable mercury.

Samples of the liquids in the reactor and two absorbers and gas leaving the reactor and leaving the two absorbers were drawn at periodic intervals over a ninety-minute period and analyzed for mercury by Lumex. Mercury balances over 57 runs average 98.6%. The reaction of the mercury chloride in the three neck flask is rapid, and the elemental mercury was stripped rapidly as well. After a typical ninety-minute period the conversion and displacement of mercury in the reactor averaged 94%.

The efficiency of the test solutions was calculated by comparing the amount of mercury taken up in the first reactor absorber to the amount taken up in both absorbers. If no mercury was taken up in the first reactor with the test solution, the efficiency was zero percent. If all the mercury was taken up in the first reactor, the efficiency was 100%. At the end of the experiments no evidence of precipitated HgS was observed in the absorbers, and the solutions were clear.

Examples 2 and 3

A 56% MEG solution was prepared by mixing 56 wt. % monoethylene glycol (MEG) in DI water. This solution, and deionized water itself, were evaluated for mercury capture. The results as presented in Table 1 show that insignificant amounts of mercury were absorbed and retained in the test solutions in the absence of complexing agents.

TABLE 1

| Experiment | Solvent | Efficiency % |
|---|---|---|
| 2 | DI Water | 0 |
| 3 | 56% MEG | 0 |

Examples 4-9

Sodium polysulfide was added in varying amounts to 56% MEG in deionized water and evaluated according to the procedure in Experiment 1. The results in Table 2 show that polysulfide is highly effective in capturing elemental mercury vapors at 1 second of contact even when the sulfur to mercury stoichiometric ratio is near 2.

TABLE 2

| Experiment | ppm $Na_2S_x$ | S/Hg Molar ratio | Efficiency % |
|---|---|---|---|
| 4 | 36 | 0.214 | 17.74 |
| 5 | 179 | 1.071 | 30.15 |
| 6 | 357 | 2.143 | 31.15 |
| 7 | 357 | 4.286 | 46.92 |
| 8 | 893 | 10.714 | 67.91 |
| 9 | 3,571 | 42.858 | 82.49 |

Examples 10-15

A series of other complexing agents were evaluated in 56% MEG solutions in deionized water. Nalmet was obtained from ONDEO NALCO of Naperville, Ill. 60563. Results are shown in Table 3:

TABLE 3

| Experiment | Agent | ppm Na2Sx | S/Hg Molar ratio | Efficiency % |
|---|---|---|---|---|
| 10 | 20% NaSH (74%) | 641 | 5.987 | 14.28 |
| 11 | Ammonium Sulfide | 996 | 7.646 | 6.00 |
| 12 | Elemental Sulfur | 866 | 7.080 | 12.97 |
| 13 | $Na_2S * 9H_2O$ | 703 | 0.942 | 10.36 |
| 14 | $Na_2S * 9H_2O$ | 3,515 | 4.708 | 1.48 |
| 15 | Nalmet | 1,056 | 0.864 | 8.42 |

Example 16-21

Various surface-active compounds were evaluated including demulsifiers (DMO24586 and DMO24074) and defoamers (DF024250 and DF024986) obtained from Baker Hughes. These were tested using 56% MEG in water at room temperature, with 179 ppm sodium polysulfide for a 2.143 molar ration of S/Hg. As shown in Example 1, without a surface-active agent, the efficiency of absorption was only about 30%. But 5 ppm of demulsifier or defoamer significantly improved the efficiency.

TABLE 4

| Example | Agent | Dosage, ppm | Efficiency % |
|---|---|---|---|
| 16 | None | 0 | 30.15 |
| 17 | None | 0 | 28.60 |
| 18 | DMO24586 | 5 | 71.92 |
| 19 | DMO24074 | 5 | 59.31 |
| 20 | DFO24250 | 5 | 42.79 |
| 21 | DFO24986 | 5 | 52.23 |

Examples 22-23

Ammonium polysulfide and sodium polysulfide are both used in refineries to control cyanides and to moderate corrosion. Using the transient method of Example 1, the efficiency of ammonium polysulfide was explored using 56% MEG in deionized water at room temperature. The efficiencies using ammonium polysulfide were high and equivalent to those from sodium polysulfide when comparisons were made at equal S/Hg stoichiometries. Samples of the solution in the first absorber were filtered through a 0.45µ filter and analyzed for mercury. Within the limits of the Lumex technique there was no significant change in the mercury content—less than 50 ppb change, showing that Hg was absorbed as a solution and not forming significant amounts of HgS precipitate.

TABLE 5

| Example | ppm $(NH_4)_2S_x$ | S/Hg Molar ratio | Efficiency % |
|---|---|---|---|
| 23 | 2,429 | 33.510 | 68.86 |
| 23 | 243 | 3.351 | 47.58 |

Examples 24

Example 1 was modified to recycle the nitrogen gas. A Cole Parmer Masterflex™ Peristaltic Pumps was used to recycle the mercury-containing nitrogen. The inlet of the pump was the outlet of the first absorber. The outlet of the pump was the inlet nitrogen stream to the reactor. The procedure began with the three-neck flask and two absorbers assembled, and with solutions in each except for the mercury chloride solution that was added to the reactor. Initially the system was operated with nitrogen only and the peristaltic pump not engaged to flush air from the system. The peristaltic pump was then started and the inlet nitrogen flow stopped. With the system operating in recycle mode, the mercury chloride solution was injected into the reactor as in Example 1. Analyses proceeded as in Example 1 for 60 minutes. At the end of 60 minutes, the peristaltic pump was stopped and the inlet nitrogen flow started. The system was purged for an additional 60 minutes. The efficiency of absorption was measured as in Example 1 by comparing the amount of mercury in the first absorber to the amounts in both absorbers.

Examples 25-33

56% MEG was evaluated with various complexing agents at room temperature and 0° C. following the procedure of Example 24. Results are shown in Table 6. The results in recycle mode surpassed those in transient mode. The efficiency of sodium polysulfide was 95% even when the S/Hg stoichiometry was 2. Efficiencies at 0° C. were reduced by operation at 0° C. when compared to room temperature, but were still much higher than values at 0° C. in the transient mode. Sodium sulfide was also active and became more active when an oxidant (1000 ppm of sodium percarbonate) was added to 703 ppm of sodium sulfide. Elemental mercury and monatomic sulfide species appear to require an oxidant for rapid reaction.

TABLE 6

| Example | Agent | Temperature | ppm Agent | S/Hg Molar ratio | Efficiency % |
|---|---|---|---|---|---|
| 25 | 1-Hexyl Mercaptan | Room T | 720 | 3.192 | 0 |
| 26 | 30% $Na_2S_4$ | Room T | 179 | 1.037 | 77.70 |
| 27 | 30% $Na_2S_4$ | Room T | 357 | 2.073 | 96.50 |
| 28 | 30% $Na_2S_4$ | 0° C. | 357 | 4.147 | 94.84 |
| 29 | 30% $Na_2S_4$ | Room T | 893 | 10.367 | 87.92 |
| 30 | 30% $Na_2S_4$ | 0° C. | 893 | 10.367 | 73.43 |
| 31 | Ditertbutyldisulfide | Room T | 799 | 4.692 | 10.46 |
| 32 | $Na_2S * 9 H_2O$ | Room T | 703 | 0.942 | 71.33 |
| 33 | $Na_2S$ + sodium percarbonate | Room T | 703 | 0.942 | 90.06 |

Examples 34-41

The Examples show the removal of aqueous Hg anions by ion-exchange and adsorption. 10 ml samples of 56% MEG containing anionic mercury were contacted with approximately 0.1 grams of various adsorbents to study the removal of mercury. The 56% MEG solution in water contained 2439 ppm ammonium polysulfide and 267 ppb mercury. The adsorbents were Darco Carbon (Aldrich 242276), Activated Carbon (Aldrich C2889), and various anion exchange resins from Siemens: A-244OH, A-464OH, A-674OH, A-714OH, and A-284C Resins. The solutions and the solid adsorbents were mixed overnight at room temperature on a rotating wheel. The mercury content of the aqueous solution was determined along with the mercury adsorbed on the solid for most samples. The % removal was calculated based on the change of the mercury content of the liquid.

TABLE 7

| Example | Solution | Adsorbent | Sol. Hg, pbb | Ads. Hg, ppb | % Removed |
|---|---|---|---|---|---|
| 34 | MEG | None | 299 | | 0.00 |
| 35 | MEG | Darco Carbon | 1.97 | 11,600 | 99.34 |
| 36 | MEG | Act. Carbon | 129 | | 56.86 |

TABLE 7-continued

| Example | Solution | Adsorbent | Sol. Hg, pbb | Ads. Hg, ppb | % Removed |
|---|---|---|---|---|---|
| 37 | MEG | A-244OH Resin | 0.53 | 27,150 | 99.82 |
| 38 | MEG | A-464OH Resin | 0.43 | 36,200 | 99.86 |
| 39 | MEG | A-674OH Resin | 0.89 | 28,900 | 99.70 |
| 40 | MEG | A-714OH Resin | 156 | 15,900 | 47.83 |
| 41 | MEG | A-284C Resin | 0.3 | 21,400 | 99.90 |

For the purposes of this specification and appended claims, unless otherwise indicated, all numbers expressing quantities, percentages or proportions, and other numerical values used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent.

As used herein, the term "include" and its grammatical variants are intended to be non-limiting, such that recitation of items in a list is not to the exclusion of other like items that can be substituted or added to the listed items. The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

The invention claimed is:

1. A method for concurrently transporting and removing a trace amount of volatile mercury in a natural gas stream extracted from a subterranean formation, comprising:
   obtaining a produced fluid containing the natural gas and produced water from the subterranean formation;
   transporting the produced fluid in a pipeline extending from a well head above the subterranean formation to a production facility;
   injecting into the pipeline carrying the produced fluid an effective amount of a hydrate inhibitor, a complexing agent and optionally at least one of a defoamer and a demulsifier;
   wherein the complexing agent extracts volatile mercury in the natural gas, forming non-volatile mercury complexes in the produced water at a temperature of $>=0°$ C., for a treated produced fluid having a concentration of hydrate particles of less than 50 volume % and a reduced concentration of volatile mercury.

2. The method of claim 1, further comprising:
separating the treated produced fluid to generate a natural gas stream having a reduced concentration of volatile mercury, and a aqueous mixture of produced water, recovered hydrate inhibitor, unreacted complexing agent, and non-volatile mercury complexes;
heating the aqueous mixture to a temperature of at least 100° C. to provide a first stream comprising water and a second stream comprising the recovered hydrate inhibitor, the unreacted complexing agent, and the non-volatile mercury complexes.

3. The method of claim 2, further comprising:
reusing the second stream for injecting into the pipeline carrying the produced fluid.

4. The method of claim 2, further comprising prior to reusing the second stream:
removing the non-volatile mercury complexes from the second stream by any of filtration, centrifugation, precipitation, distillation, adsorption, ion exchange, and combinations thereof.

5. The method of claim 1, wherein the pipeline is at least 2.5 km.

6. The method of claim 1, wherein the demulsifier is selected from polyamines, polyamidoamines, polyimines, condensates of o-toluidine and formaldehyde, quaternary ammonium compounds, ionic surfactants, polyoxyethylene alkyl phenols, and mixtures thereof.

7. The method of claim 1, wherein the produced fluid being transported in the pipeline has a superficial liquid velocity of at least 0.1 m/s.

8. The method of claim 1, wherein the complexing agent is selected from water-soluble sulfur compounds, mercaptans, organic polysulfides, sulfanes, and mixtures thereof.

9. The method of claim 8, wherein the water-soluble sulfur compound is selected from sodium polysulfide, ammonium polysulfide, calcium polysulfide, sodium hydrosulfide, potassium hydrosulfide, ammonium hydrosulfide, sodium sulfide, potassium sulfide, calcium sulfide, magnesium sulfide, ammonium sulfide, sodium thiocarbamate, sodium dithiocarbamate, ammonium thiocarbamate and ammonium dithiocarbamate, and mixtures thereof.

10. The method of claim 9, wherein the water-soluble sulfur compound is sodium polysulfide.

11. The method of claim 1, wherein at least 50% of the volatile mercury is removed from the natural gas in the pipeline.

12. The method of claim 10, wherein at least 90% of the volatile mercury is removed from the natural gas.

13. The method of claim 1, wherein the natural gas in the treated produced fluid contains less than 100 µg/Nm$^3$ mercury.

14. The method of claim 13, wherein the natural gas in the treated produced fluid contains less than 10 µg/Nm$^3$ mercury.

15. The method of claim 13, wherein the natural gas in the treated produced fluid contains less than 1 µg/Nm$^3$ mercury.

16. The method of claim 14, wherein the natural gas in the treated produced fluid contains less than 0.1 µg/Nm$^3$ mercury.

17. The method of claim 1, wherein the hydrate inhibitor is a thermal inhibitor and the effective amount of the thermal inhibitor ranges from 5-80 vol % of the produced water in the pipeline.

18. The method of claim 1, wherein the hydrate inhibitor is a low dose hydrate inhibitor and the effective amount of the low dose hydrate inhibitor ranges from 0.5-5.0 vol % of the produced water in the pipeline.

19. The method of claim 1, wherein the complexing agent is injected into the pipeline at a molar ratio of complexing agent to heavy metals ranging from 1:1 to 10,000:1.

20. The method of claim 19, wherein the complexing agent is injected into the pipeline at a molar ratio of complexing agent to heavy metals ranging from 2:1 to 5,000:1.

21. The method of claim 19, wherein the complexing agent is injected into the pipeline in an amount of up to 5 vol. % of the produced water in the pipeline.

22. The method of claim 21, wherein the complexing agent is injected into the pipeline in an amount of up to 2 vol. % of the produced water in the pipeline.

23. The method of claim 1, wherein the complexing agent is selected from alkali sulfides, alkali hydrosulfides, ammonium sulfides, sodium polysulfide, ammonium polysulfide, calcium polysulfide and mixtures thereof, and wherein volatile mercury is extracted into the produced water forming soluble mercury complexes.

* * * * *